United States Patent
Flanders

(10) Patent No.: US 7,509,156 B2
(45) Date of Patent: Mar. 24, 2009

(54) SYSTEM FOR MANAGING GLUCOSE LEVELS IN PATIENTS WITH DIABETES OR HYPERGLYCEMIA

(75) Inventor: Samuel J. Flanders, Indianapolis, IN (US)

(73) Assignee: Clarian Health Partners, Inc., Indianapolis, IN (US)

( * ) Notice: Subject to any disclaimer, the term of this patent is extended or adjusted under 35 U.S.C. 154(b) by 592 days.

(21) Appl. No.: 11/131,707

(22) Filed: May 18, 2005

(65) Prior Publication Data
US 2006/0264895 A1 Nov. 23, 2006

(51) Int. Cl.
*A61B 5/05* (2006.01)

(52) U.S. Cl. .................. 600/347; 600/365; 604/66; 604/504

(58) Field of Classification Search ............... 604/66, 604/504; 600/347, 365
See application file for complete search history.

(56) References Cited

U.S. PATENT DOCUMENTS

| | | | | | |
|---|---|---|---|---|---|
| 3,837,339 | A | * | 9/1974 | Aisenberg et al. | 604/504 |
| 4,515,584 | A | * | 5/1985 | Abe et al. | 604/66 |
| 4,526,569 | A | * | 7/1985 | Bernardi | 604/6.09 |
| 4,538,616 | A | * | 9/1985 | Rogoff | 600/365 |
| 4,633,878 | A | * | 1/1987 | Bombardieri | 600/347 |
| 4,634,426 | A | | 1/1987 | Kamen | |
| 5,474,552 | A | * | 12/1995 | Palti | 604/67 |
| 5,820,622 | A | * | 10/1998 | Gross et al. | 604/890.1 |
| 6,572,545 | B2 | | 6/2003 | Knobbe et al. | |
| 6,736,801 | B1 | | 5/2004 | Gallagher | |
| 6,835,175 | B1 | * | 12/2004 | Porumbescu | 600/300 |
| 7,163,511 | B2 | * | 1/2007 | Conn et al. | 600/309 |
| 7,267,665 | B2 | * | 9/2007 | Steil et al. | 604/131 |
| 2002/0130779 | A1 | | 9/2002 | Ford | |
| 2003/0027089 | A1 | | 2/2003 | Galley et al. | |
| 2003/0036683 | A1 | * | 2/2003 | Kehr et al. | 600/300 |
| 2004/0143346 | A1 | | 7/2004 | Francis et al. | |
| 2005/0038674 | A1 | * | 2/2005 | Braig et al. | 705/2 |

FOREIGN PATENT DOCUMENTS

| | | |
|---|---|---|
| CA | 1040271 | 10/1978 |
| CA | 1283206 | 4/1991 |
| DE | 19844252 | 3/2000 |
| EP | 0834825 | 4/1998 |
| GB | 2153081 | 8/1985 |

OTHER PUBLICATIONS

Goldberg et al., *Implementation of a Safe and Effective Insulin Infusion Protocol in a Medical Intensive Care Unit*, Diabetes 52 (Suppl. 1):A104, 2003.
Bode et al., *Intravenous Insulin Infusion Therapy: Indications, Methods and Transition to Subcutaneous Insulin Therapy*, Endocrine Practice, vol. 10 (Suppl 2) Mar./Apr. 2004 71-80.

\* cited by examiner

*Primary Examiner*—Robert L Nasser
*Assistant Examiner*—Karen E Toth
(74) *Attorney, Agent, or Firm*—Woodard, Emhardt, Moriarty, McNett & Henry LLP, Patent and Trademark Attorneys

(57) ABSTRACT

A blood glucose maintenance system for use by hyperglycemic individuals measures their blood glucose level and calculates an appropriate glucose or insulin dosage based on the measurement. Recheck intervals responsive to dosage history are determined. Warning or alert messages or signals are produced if certain measurements or calculations fall outside established normal ranges. It is particularly useful for patients in a hospital or in-patient environment.

3 Claims, 26 Drawing Sheets

FIGURE 4

```
┌─────────────────────────────────────────────────────────────────┐
│ DO NOT CLOSE THIS WINDOW                              _ □ ×     │
│                                                                  │
│              INSULIN INFUSION PROGRAM              V2.1          │
│                                                                  │
│            01/10/2005     Run #   0      17:48:55                │
│                                                                  │
│ ┌RUN_NO─┬─PTNAME──────────────┬─PT RECNO─┬─DATE──────┬─TIME─────┬─HOS─┐
│ │  43   │ DOE, JOHN           │  33333   │01/10/2005 │17:44:00  │ YES │
│ └───────┴─────────────────────┴──────────┴───────────┴──────────┴─────┘
│                                                                  │
│   1) Enter Glucose              6) Browse/Print Infusion History │
│   2) Start New Insulin Drip     7) Change Drip Setup             │
│   3) Resume Prior Drip          8) Erase last Glucose/Orders     │
│   4) Print Orders               9) Run report to assist drip weaning │
│   5) Stop/Hold Drip and EXIT PROGRAM                             │
│                                                                  │
│  Use arrow keys to highlight. ENTER to select. ESC to abort. F9 to Zoom │
└─────────────────────────────────────────────────────────────────┘
```

201

```
┌─────────────────────────────────────────────────────────────────┐
│ ▣ DO NOT CLOSE THIS WINDOW                          _ ☐ ✕       │
│                                                                 │
│            INSULIN INFUSION PROGRAM              V2.1           │
│                                                                 │
│            01/10/2005    Run #   43     17:35:58                │
│                                                                 │
│                    ┌─────────────────────┐                      │
│                    │  INSULIN DRIP SETUP │                      │
│                    └─────────────────────┘                      │
│                                                                 │
│          PTNAME   : DOE, JOHN                                   │
│                                                                 │
│          Patient Name (Last, First)                             │
│                                                                 │
│                                                                 │
│   1) Enter Glucose              6) Browse/Print Infusion History│
│   2) Start New Insulin Drip     7) Change Drip Setup            │
│   3) Resume Prior Drip          8) Erase last Glucose/Orders    │
│   4) Print Orders               9) Run report to assist drip weaning
│   5) Stop/Hold Drip and EXIT PROGRAM                            │
└─────────────────────────────────────────────────────────────────┘
```

```
INSULIN INFUSION PROGRAM                    V2.1
      01/10/2005    Run #   43    17:35:58

INSULIN DRIP SETUP

NEW BGCOUNT: 3 of BGs before going to routine BG time

1) Enter Glucose              6) Browse/Print Infusion History
2) Start New Insulin Drip     7) Change Drip Setup
3) Resume Prior Drip          8) Erase last Glucose/Orders
4) Print Orders               9) Run report to assist drip weaning
5) Stop/Hold Drip and EXIT PROGRAM
```

```
                INSULIN INFUSION PROGRAM                          V2.1

01/10/2005        Run #   43      17:32:01

CURRENT ORDERS AS OF 01/10/2005 @ 17:31
Start Insulin Infusion at  4.7 Units/hour.  Multiplier = 0.02
Do next blood glucose in   60 minutes INSULIN INFUSION STATUS:
Insulin infusion running at  4.7 Units/hour.  Last BG =  295
Next Blood Glucose due at 18:31.

TYPE A SELECTION:
  1) Enter Glucose                    6) Browse/Print Infusion History
  2) Start New Insulin Drip           7) Change Drip Setup
  3) Resume Prior Drip                8) Erase last Glucose/Orders
  4) Print Orders                     9) Run report to assist drip weaning
  5) Stop/Hold Drip and EXIT PROGRAM
```

INSULIN INFUSION PROGRAM V2.1

01/10/2005  Run # 43  17:34:42

| DATE | TIME | GLUCOSE | MULTIPLIER | DRIPRATE | D50MLS | LOWTARGET | HITARGET | COMM |
|------|------|---------|------------|----------|--------|-----------|----------|------|
| 01/10/2005 | 17:31:52 | 295 | 0.02 | 4.7 | 0 | 80 | 110 | This |
| 01/10/2005 | 17:33:15 | 250 | 0.03 | 5.7 | 0 | 80 | 110 | |
| 01/10/2005 | 17:33:27 | 201 | 0.04 | 5.6 | 0 | 80 | 110 | |
| 01/10/2005 | 17:34:08 | 150 | 0.05 | 4.5 | 0 | 80 | 110 | |
| 01/10/2005 | 17:34:21 | 100 | 0.05 | 2.0 | 0 | 80 | 110 | |
| 01/10/2005 | 17:34:31 | 65 | 0.04 | 0.2 | 14 | 80 | 110 | |
| 01/10/2005 | 17:34:41 | 99 | 0.04 | 1.6 | 0 | 80 | 110 | |

1) Enter Glucose
2) Start New Insulin Drip
3) Resume Prior Drip
4) Print Orders
5) Stop/Hold Drip and EXIT PROGRAM 6) Browse/Print Infusion History
7) Change Drip Setup
8) Erase last Glucose/Orders
9) Run report to assist drip weaning Press <ESC> when done.  F9 to ZOOM.

178

```
INSULIN DRIP CONVERSION TO SUBCUTANEOUS INSULIN

Patient=DOE, JOHN              MRN=33333           Room=135
Hospital=TE  Nursing Unit=TEST     Printed on 01/10/2005 @ 17:47:49
Most recent drip data: Date:01/10/2005  Time:17:44:00  BG: 87  Mult: 0.04
Drip has been stable for    0.2 hours  WARNING: MAY NOT BE ENOUGH TIME
Total Daily Dose of Insulin (estimate) =    47 Units/Day
1 Unit of Insulin should lower the BG by approximately    36 mg/dl
1 Unit of Insulin should cover approximately  11 Grams of dietary carbohydrate NOTE: These are only estimates.  They may not be accurate if the patient:
      -has not had a constant, consistent source of carbohydrate
      -is on pressors
      -is getting any additional insulin besides the drip (in TPN, Glargine, etc.)

Press any key to continue...
```

FIGURE 26

SYSTEM FOR MANAGING GLUCOSE LEVELS IN PATIENTS WITH DIABETES OR HYPERGLYCEMIA

FIELD OF THE INVENTION

This invention relates to maintenance of proper glucose levels in hyperglycemic individuals, and in particular, to a system that aids in the correct administration of insulin through the use of computerized insulin dosage calculations that are made with the use of individual-specific information.

BACKGROUND OF THE INVENTION

Maintaining proper blood sugar, i.e., glucose, levels is important for hyperglycemic individuals, e.g., diabetics, in order to prevent long term problems such as nerve damage, blindness, and kidney disease. The need to control blood glucose (often referred to as BG) levels is even more important with hyperglycemic patients in critical care situations, such as in hospital intensive care units following surgical procedures, as those patients are more likely to suffer adverse physical effects, e.g., infections, from improperly maintained BG levels. Compounding this problem is the fact that BG levels in such patients may be unstable, necessitating frequent measurements and adjustments of administered insulin dosage. At times the degree of insulin dosage adjustment may be significant, or the calculated dosage amount may be high, so that it is difficult to determine whether the calculated insulin dose is correct or if an error in blood sugar measurement or an equipment malfunction has occurred.

SUMMARY OF THE INVENTION

It is therefore an object of one embodiment of the present invention to provide a system for monitoring patients' blood glucose levels, calculating proper insulin dosages, and providing relevant feedback information and messages to the individual, or when used in a hospital or other in-patient setting, to the patient's physician, nurse, or other caregiver. Variations of BG levels outside a predetermined range results in more frequent BG measurements, while calculated insulin doses that fall outside normally expected levels (either high or low) generate feedback messages and warnings that require additional measurement or caregiver intervention to insure the correct treatment is administered.

BRIEF DESCRIPTION OF THE DRAWING

FIGS. 4 through 27 are representative computer screen images illustrating aspects of the operation of a blood glucose management system in accordance with an embodiment of the present invention.

DETAILED DESCRIPTION

Figure 1:
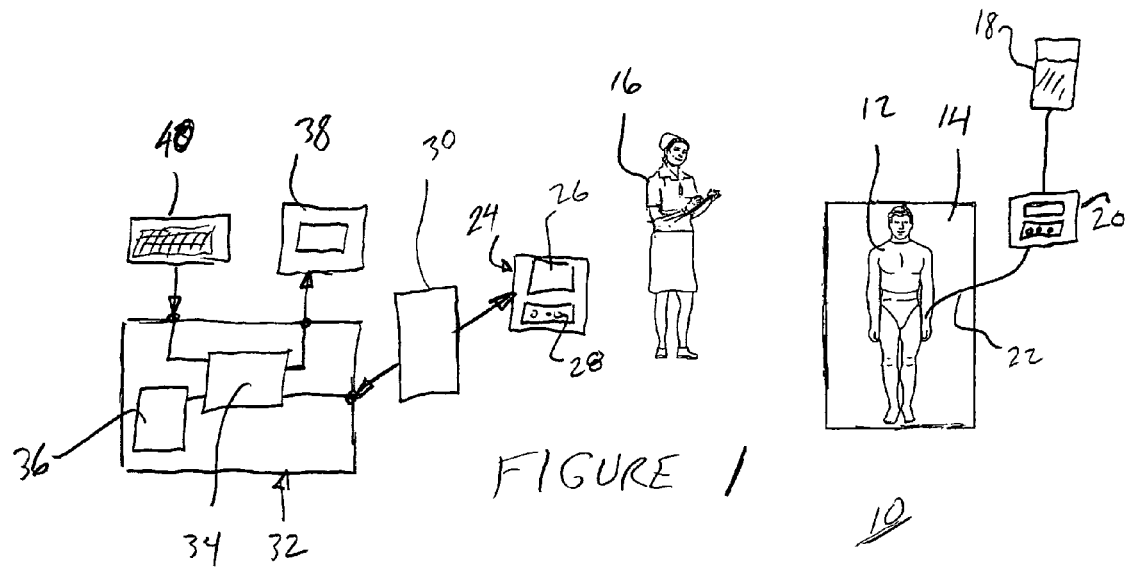
FIG. 1 is a diagrammatic view of a blood glucose management system in accordance with one embodiment of the present invention.

For the purposes of promoting understanding of the principles of the invention, reference will now be made to the embodiments illustrated in the drawings and specific language will be used to describe the same. It will nevertheless be understood that no limitation of the scope of the invention is hereby intended and alterations and modifications in the devices, systems and representations illustrated in the Figures of the drawing, and further applications of the principles of the present invention as illustrated herein being contemplated as would normally occur to one skilled in the art to which the invention relates.

Referring to FIG. 1, there is shown a blood glucose (BG) management system 10 for a hyperglycemic patient 12 who is illustratively being cared for in a hospital critical care setting, e.g., within an intensive care unit following heart surgery, although other patient settings are of course possible. The condition of patient 12 on bed 14 is shown as being illustratively monitored directly by a nurse or caregiver 16, but at least some functions that are performed by nurse 16 could be performed by automatic monitoring (pulse, blood pressure), data entry, and/or intravenous medication delivery equipment (not shown), to name only a few possible examples. For purposes of explaining an embodiment of the present invention, patient 12 is shown as receiving a continuous drip of insulin from reservoir 18 that is controlled by drip regulator 20 through an intravenous (IV) line 22.

In operation, nurse 16 tests the blood sugar or glucose level of patient 12 by a known, available means including, but not limited to, a traditional finger stick using known, commercially available products. Nurse 16 then enters the measured BG level of patient 12 into data handling device 24. Device 24 is illustratively shown as having a display 26 and an input 28. Display 26 may be of any conventional or available display type, such as, for example, a CRT or LCD screen, while input 26 may be a computer keyboard, for example. When the patient's measured glucose level has been entered into device 24, the entered information is sent via communications channel 30 to computer or data processor 32 which may be located at a central location, such as a nurses' station or hospital-wide patient monitor center. Communications channel 30 may be of the form of a hardwired connection, a local area network, or an internet-based wide area network, to cite a few non-limiting examples. Network access may advantageously provide access to patient data from other hospitals or in-patient facilities, and it can allow patent 12 to be moved within a networked facility or between network-linked facilities, while still maintaining active monitoring of the patient's condition and providing access to historical patient data. Data processor 32 illustratively comprises a central processing unit (CPU) 34 and memory 36, which may be of any known or available form, such as, for example, ROM, PROM, RAM, EPROM or EEPROM. Also shown as being connected or associated with data processor 32 are display 38 (such as, for example, a CRT or LCD screen) and input device 40, such as a keyboard, for example.

Data processor 32 evaluates the BG level of patient 12 to determine if the glucose level is high or low. If it is low, data processor 32 calculates an appropriate dosage of glucose, typically administered as dextrose (such as that identified as D-50), that is needed to bring the BG level of patient 12 back within a predetermined "normal" range. If the BG level is high, data processor 32 calculates a proper insulin drip level that required to restore the BG level of patient 12 to the "normal" range. If the BG level is within the "normal" range for patient 12, data processor 32 calculates a proper insulin drip level sufficient to maintain the BG level of patient 12 within the "normal" range. The information is sent back to device 24 via communications channel 30 where it appears on display 26. Nurse or caregiver 16 then administers dextrose, if needed, or makes any necessary adjustments to drip regulator 20 so that the proper amount of insulin 18 is delivered to patient 12. The calculation used by CPU 34 of data processor 32 illustratively utilizes a known algorithm identified as the *Protocol of Bode* et al., and described in an article entitled "Intravenous Insulin Infusion Therapy: Indications, Methods, and Transition to Subcutaneous Insulin Therapy," Endocrine Practice, Vol. 10 (Suppl. 2), March/April 2004, but a proprietary algorithm or some other proven calculation could be developed or adapted to be suitable as well.

Figure 2:
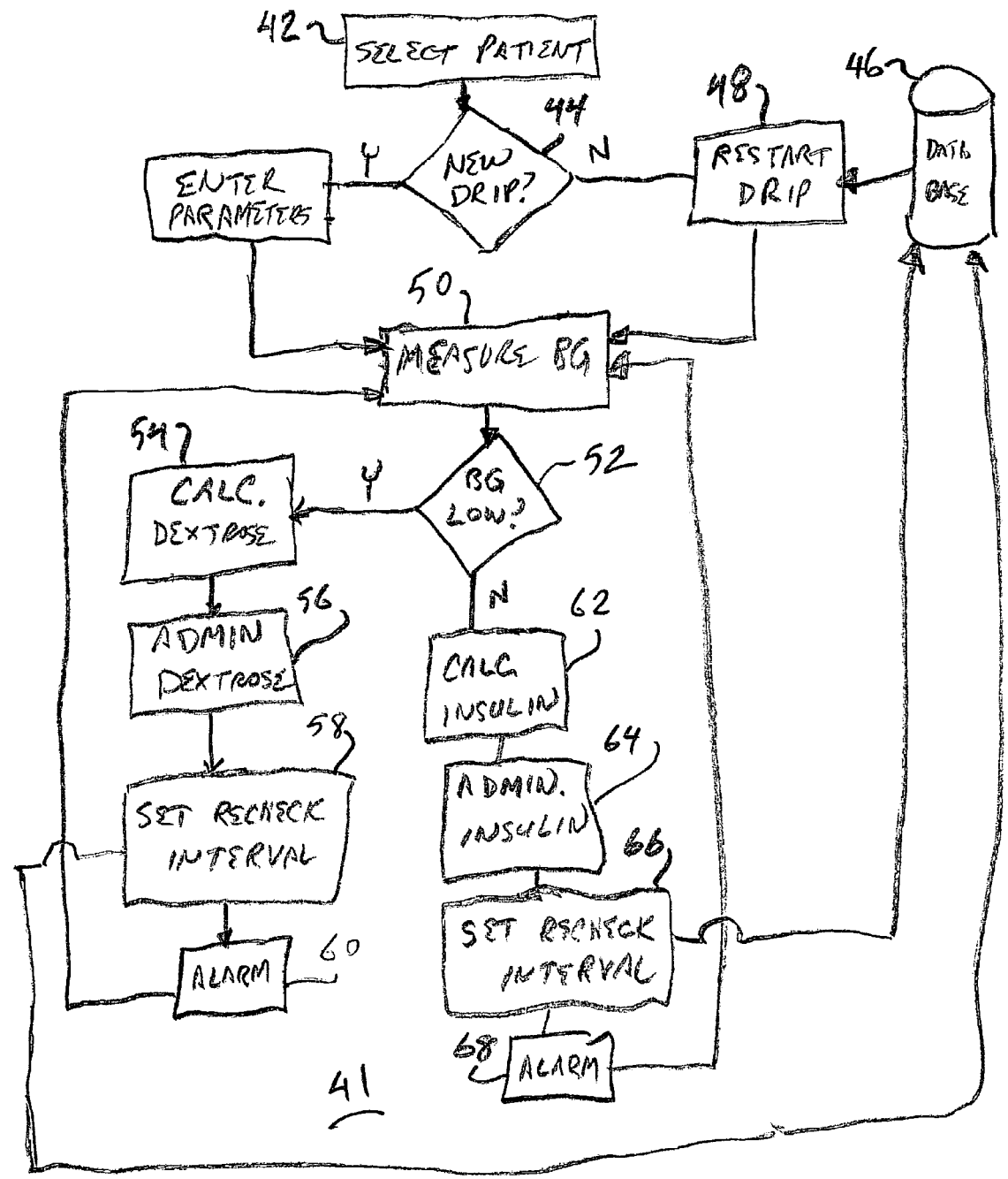
FIG. 2 is a flowchart illustrating the operation of a blood glucose management system in accordance with an aspect of the present invention.

FIG. 2 illustrates a flowchart which shows a BG management process 41 in accordance with an embodiment of the present invention, which will be used to illustrate the manner in which BG management system 10 of FIG. 1 operates. Beginning at step 42 of process 41, a particular patient is selected for BG monitoring or management by system 10. For illustrative purposes, the process of step 42 selects critical care patient 12. Step 44 determines from information provided by step 42 whether patient 12 requires a new insulin drip to be established, or whether a previously established insulin drip is to be restarted. If the drip is to be restarted, information concerning the previous insulin drip for patient 12 is retrieved from database 46 and used in step 48 to set initial insulin administration, e.g., drip rate, multiplier and "normal" BG level, data for patient 12. Having access to known information specific to patient 12 greatly aids in establishing an initial insulin drip rate that will be more accurate, and hence lead to a quicker stabilization of the BG level for patient 12 than would be possible if a drip rate were started from a nominal average value. Access to this information allows patient 12 to be temporarily discontinued from a drip without requiring a "break-in" period when the drip is resumed. If patient 12 is a new patient, or if information related to a previous drip is no longer valid, certain initial parameters, such as high and low target BG levels that establish a "normal" range for patient 12, are set and stored in database 46. Process 41 then proceeds to step 50, which measures the BG level of patient 12. In FIG. 1, the BG level of patient 12 is measured manually by nurse 14, and entered into data handling device 24, which communicates that information to data processor 32. Process 41, including step 50, need not be performed manually by a nurse or caregiver, but could be performed automatically without human intervention. The measured BG level is then evaluated at step 52 to determine if the BG level falls below, within, or above the "normal" range previously established for patient 12.

If the measured BG level is low (i.e., below the lower limit of the desired BG range), step 54 calculates the appropriate amount of glucose (e.g., D-50 dextrose) needed by patient 12. This information is used by process 41 at step 56 to administer the dextrose dose to patient 12. Process 41 then sets an appropriate recheck interval at step 58, e.g., 15 minutes, at which time alarm 60 either provides an audible or visible alert to nurse 16 that it is time to recheck the BG level of patient 12. In an automated arrangement, alarm 60 could initiate a new BG check via step 50 directly. The information determined at step 58 is also stored in database 46 to provide historical data that can be used to generate a complete report about patient 12, re-establish a drip, or more accurately predict the course of treatment needed to control BG levels in patient 12.

If the evaluation at step 52 determines that the BG level is high (i.e., above the upper limit of the desired BG range), process 41 calculates the proper insulin drip rate for patient 12 at step 62. This insulin dosage is then administered at step 64, which permits adjustment of the insulin drip rate and volume being given to patient 12 based on the information determined at step 62. At step 66, process 41 then determines an appropriate BG level recheck interval (that is also stored in database 46) for patient 12. At the end of such interval, alarm 68 provides an alert to a nurse or caregiver that it is time to recheck the BG level of patient 12 or, in an automated system or environment, directly initiates a BG level measurement via step 50.

Process 41 may incorporate additional alerts that require additional evaluations or determinations in order to proceed, so that improper measurements or data entry, or an equipment malfunction, may be discovered before an incorrect treatment is administered to a patient. Such alerts may, for example, be associated with step 50 if the BG level measured at a given time is significantly different than that measured previously, or if the previous measurement was done only a short time before. Alerts could also be associated with steps 54 or 62 if the calculated dextrose or insulin dosage amount appears to be abnormally high or low. Other alert mechanisms may also be included as desired and the actions needed, e.g., doctor or nurse sign-off, BG level recheck, may be specified in order for the process to proceed. Process 41 can use the information stored in database 46, which creates a permanent archived record for each patient, to create individual patient reports or to determine trends and predictions from statistically analyzing a large amount of data from a number of patients.

Many of the functions of system 10 that have been described with reference to FIG. 2 may be performed by electronic circuitry and/or with computer software, including but not limited to the steps of determining whether measured or calculated amounts are within normal ranges, issuing alert messages, and setting patient glucose level recheck intervals. Such automation is clearly much more important in an outpatient environment (e.g., diabetics utilizing insulin pumps) than with an in-patient situation where continuous or frequent nursing or other medical care is provided.

Figure 3:
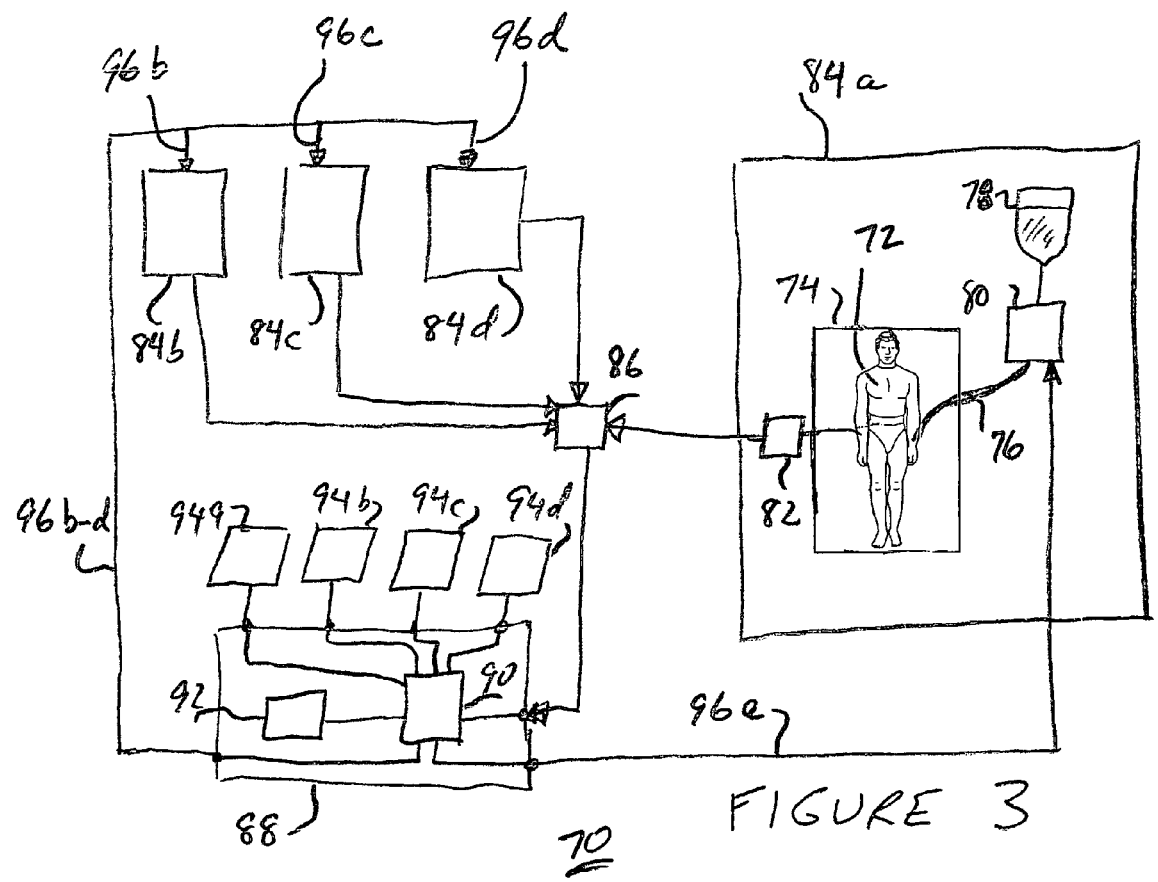
FIG. 3 is a diagrammatic view of a blood glucose management system in accordance with another embodiment of the present invention.

FIG. 3 shows a BG management system 70 that is adapted to handle multiple or even large numbers of patients, and that automatically performs certain functions that were done manually or with human intervention in system 10 of FIG. 1. It is understood, however, that the number of patients and the degree of automation are shown and described for illustrative purposes only, and the aspects and advantages of the present invention are not dependent upon any particular number of patients or the manner in which the operating steps are performed.

System 70 operates similarly to system 10 of FIG. 1 in that an illustrative patient 72, located on bed or other device 74 in a hospital or other in-patient facility, is administered an insulin drip via IV tube 76 from insulin reservoir 78, with the rate and amount of that drip being set by drip controller 80. The BG level of patient 72, however, is measured automatically by measurement device 82, rather than manually as was done as by nurse 16 in system 10 shown in FIG. 1. For the sake of a more simplified explanation of system 70, the above-described elements associated with patient 72 can be considered to make up an overall patient unit 84a.

FIG. 3 illustratively shows additional patient units 84b, 84c, and 84d, although it is understood that any number of patient units may be provided. The automatically measured BG levels from each of patient units 84a-d is applied to controller 86 which coordinates data from the various patient units. The data is provided to data processor 88 in a manner that enables data processor 88 to identify the patient unit that is the source of each piece of information. It is understood that the functionality of controller 86 may be incorporated in some other component such that an identifiable discrete element may not be present. Data processor 88 illustratively incorporates a central processing unit (CPU) 90 and a memory unit 92, which may be of any known or otherwise appropriate type. Also shown as being associated with data processor 88 are input/output (I/O) devices 94*a-d*, which illustratively correspond to patient units 84*a-d* respectively. It is of course possible that a single or limited number of I/O devices may be provided so that multiple patient units can be accommodated by one I/O device in a multiplexed fashion. Insulin drip rate information is provided to the corresponding drip controllers in each of patient units 84*a-d* via output lines 96*a-d*.

The operation of system 70 in FIG. 3 may also be represented by the process that is shown and described in connection with FIG. 2. Alert signals may be evaluated by automatic failsafe or double checking circuitry, or a human intervener, such as the equivalent of nurse 16, may be called upon to verify the accuracy of measurements or calculations if they do not appear to fall within "normal" or previously measured limits.

FIGS. 4 through 26 will now be described as illustrative examples of representative display screens for a computer software program that performs certain of the functions described in connection with system 10 and/or system 70. For the sake of efficiency and readability in describing FIGS. 4 through 26, reference will be made solely to system 10, although it is understood that references to the operation of system 10 are also applicable to system 70 whenever such described function is performed by system 70.

Figure 5:
Figure 7:
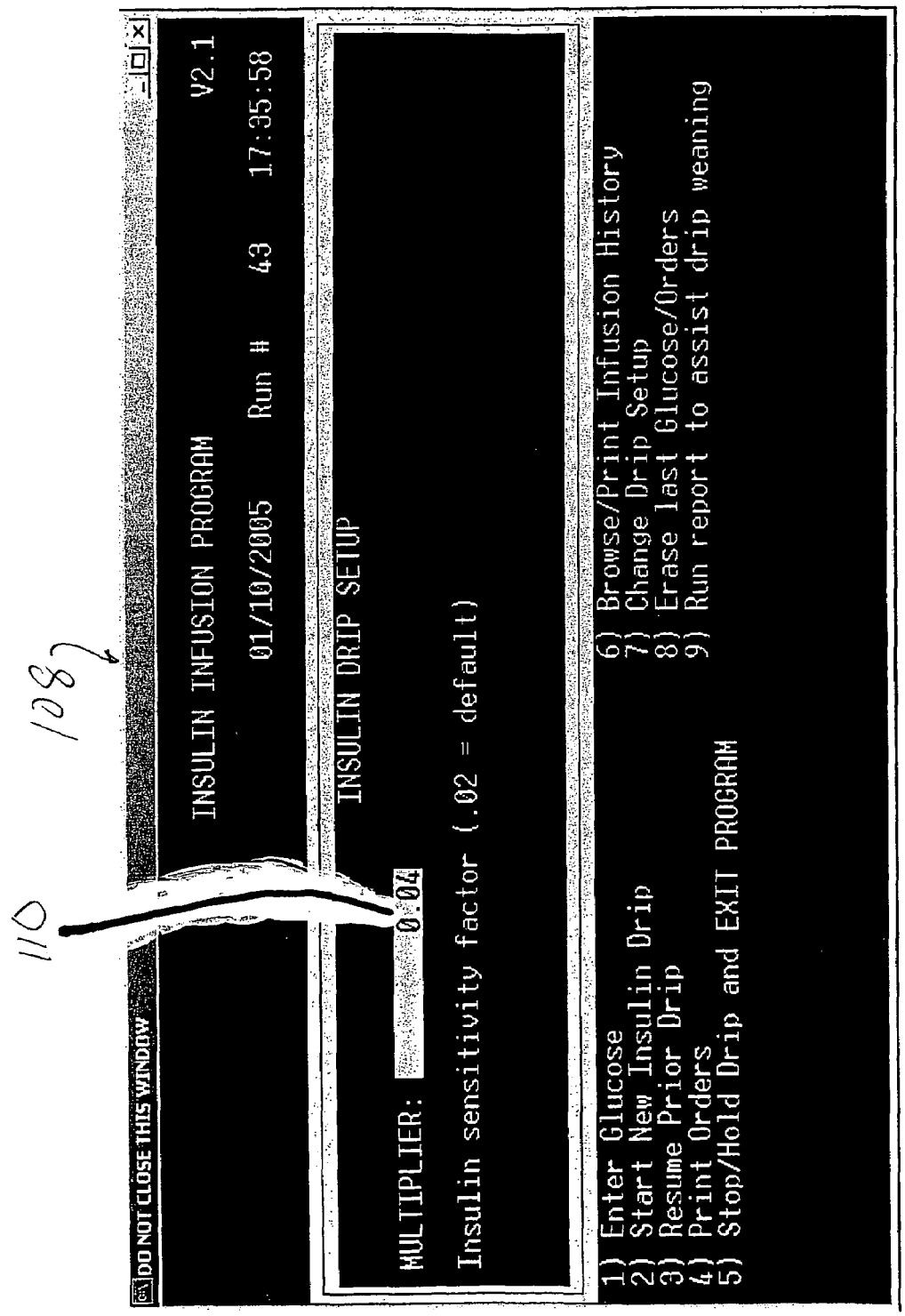
Figure 8:
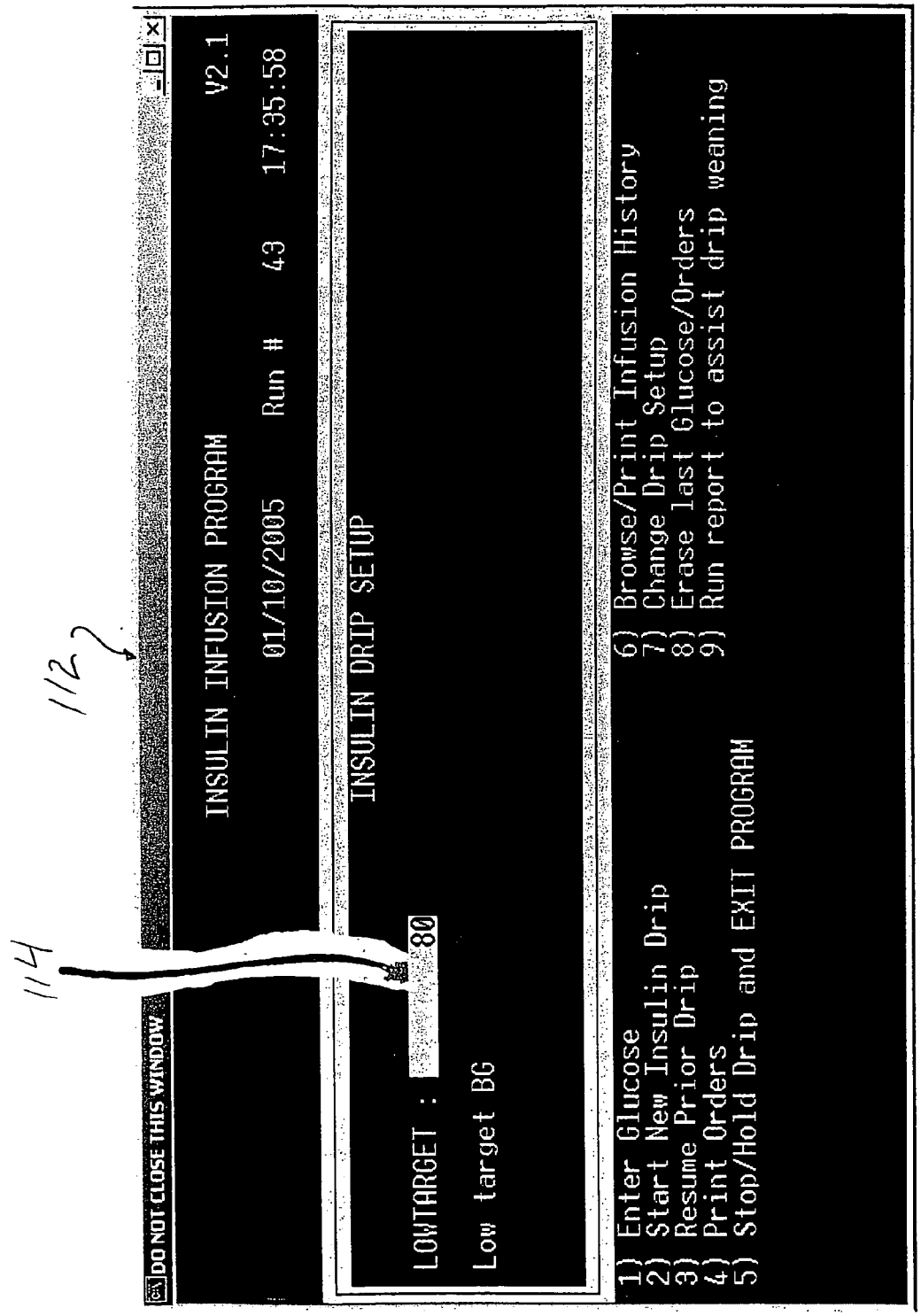
Figure 9:
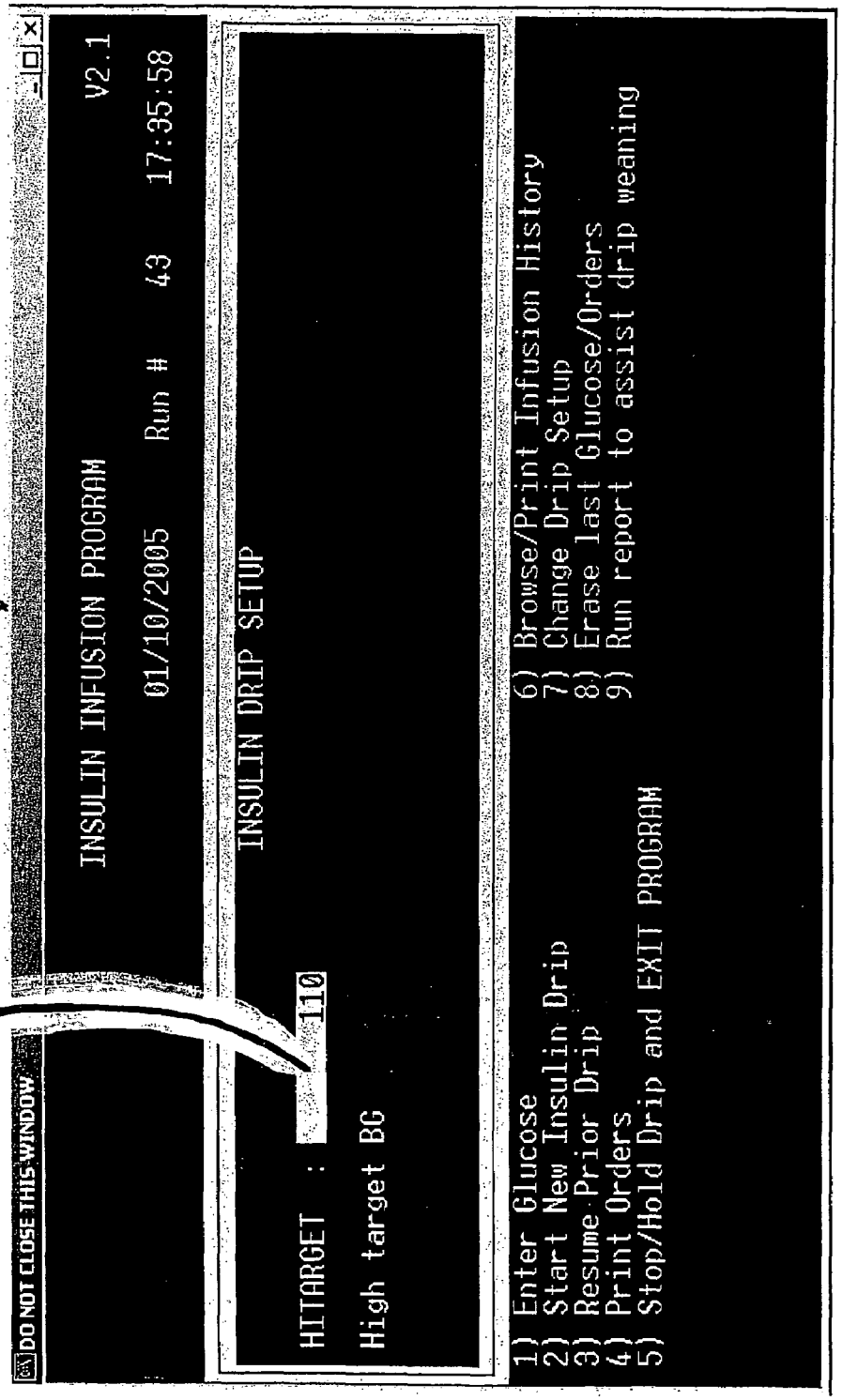

FIG. 4 illustrates one example of an initial system status screen 100 that identifies all patients that are under the control of blood glucose management system 10 (in this case only John Doe), with each patient's identification number as well as other data. It is understood that the information provided on screen 100 is shown for illustrative purposes, and other types of information, such as the ages of the patients, their room number, and medication list, for example, could also be shown. Screen 100 further provides a list of possible actions that may be taken with respect to a given patient, including the action of resuming a previous, e.g., temporarily discontinued, drip, or starting a new drip. If the action to resume a prior drip is selected, for example, a screen (not shown) might then be displayed to verify that the action of resuming a prior drip was intended to be selected. FIG. 5 shows a display screen 102 that displays an alert message 104 in response to a selection of the function Change Drip Setup. The alert message requires a response as to whether previously entered insulin drip setup parameters are to be changed. FIG. 6 illustrates a screen 106 that illustratively appears in response to a decision to change drip setup parameters for a selected patient, i.e., John Doe. FIGS. 7 through 20 illustrate a series of screens that requests specific information that system 10 will use to determine insulin drip rates for patient John Doe. The information provided for John Doe would therefore be expected to be different than corresponding information for other patients. By way of example, FIG. 7 shows a screen 108 that requires the entry of a number 110 representing the selected patient's (John Doe's) insulin sensitivity factor. FIG. 8 shows a screen 112 requesting an entry 114 of the BG level that is desired to be the lower limit of John Doe's target "normal" glucose level range (in this case 80 mg/dl), while FIG. 9 shows a screen 116 requesting an entry 118 of the BG level that is desired to be the upper limit of John Doe's target glucose level range (in this case 110 mg/dl).

Figure 10:
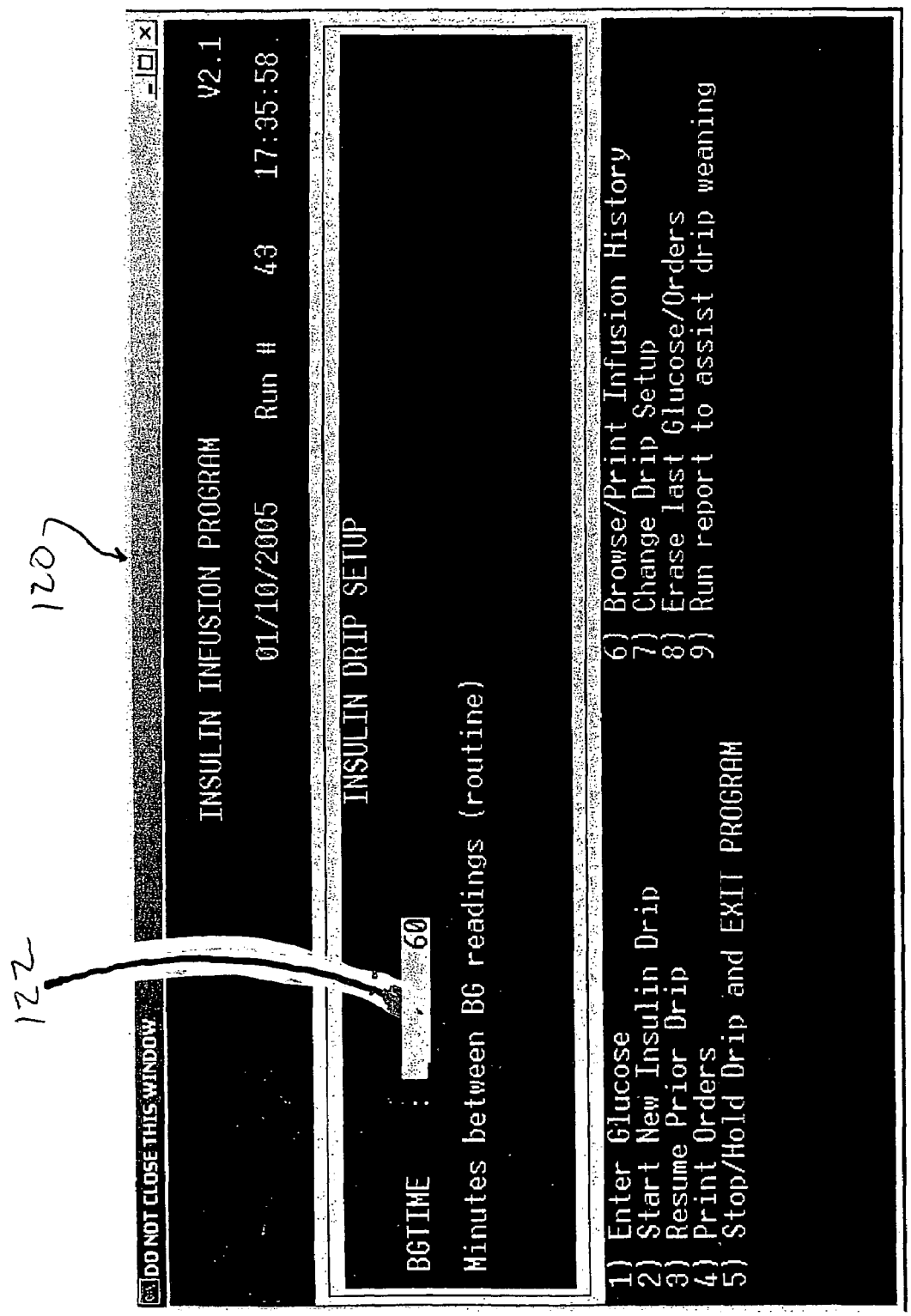
Figure 11:
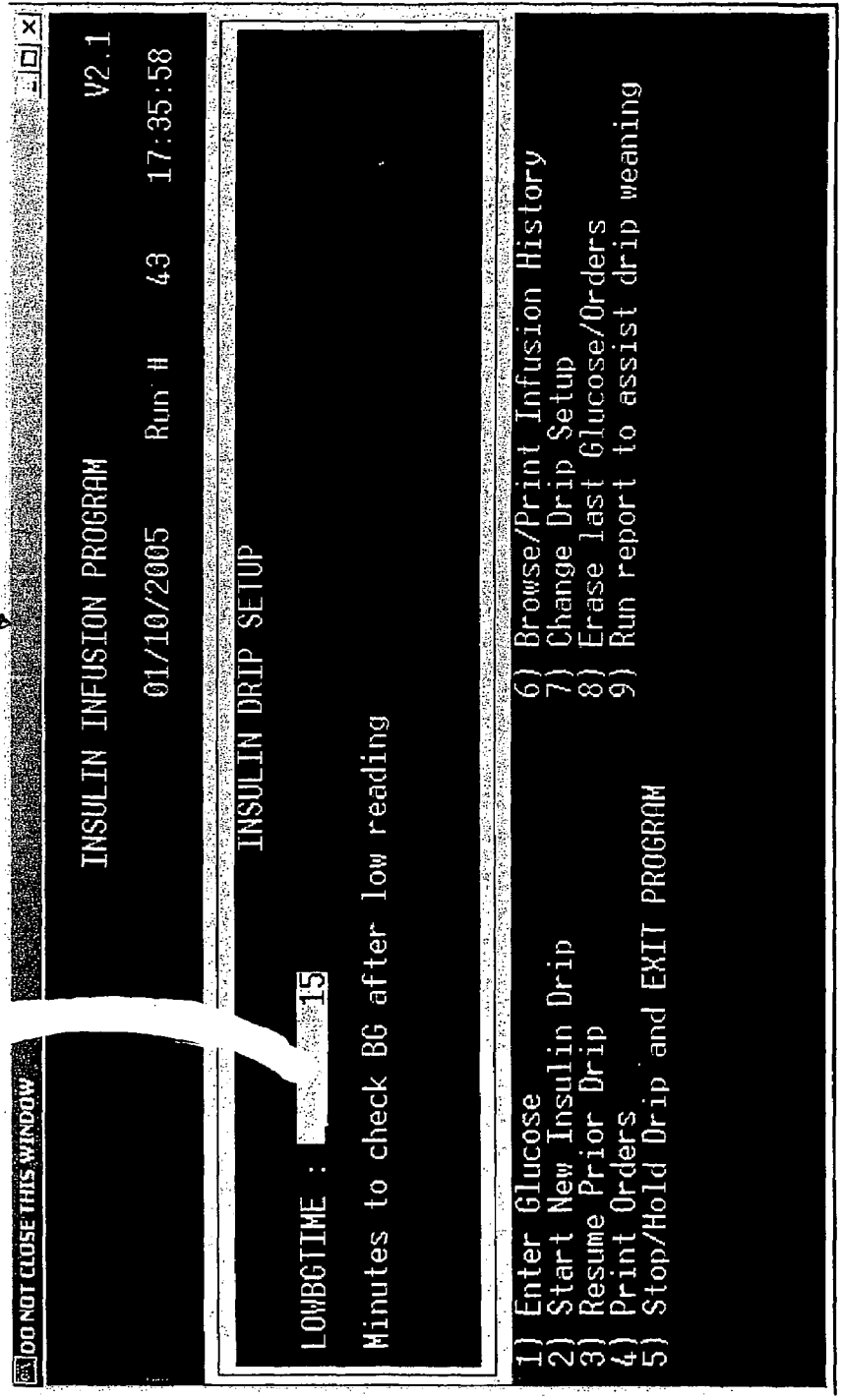
Figure 13:
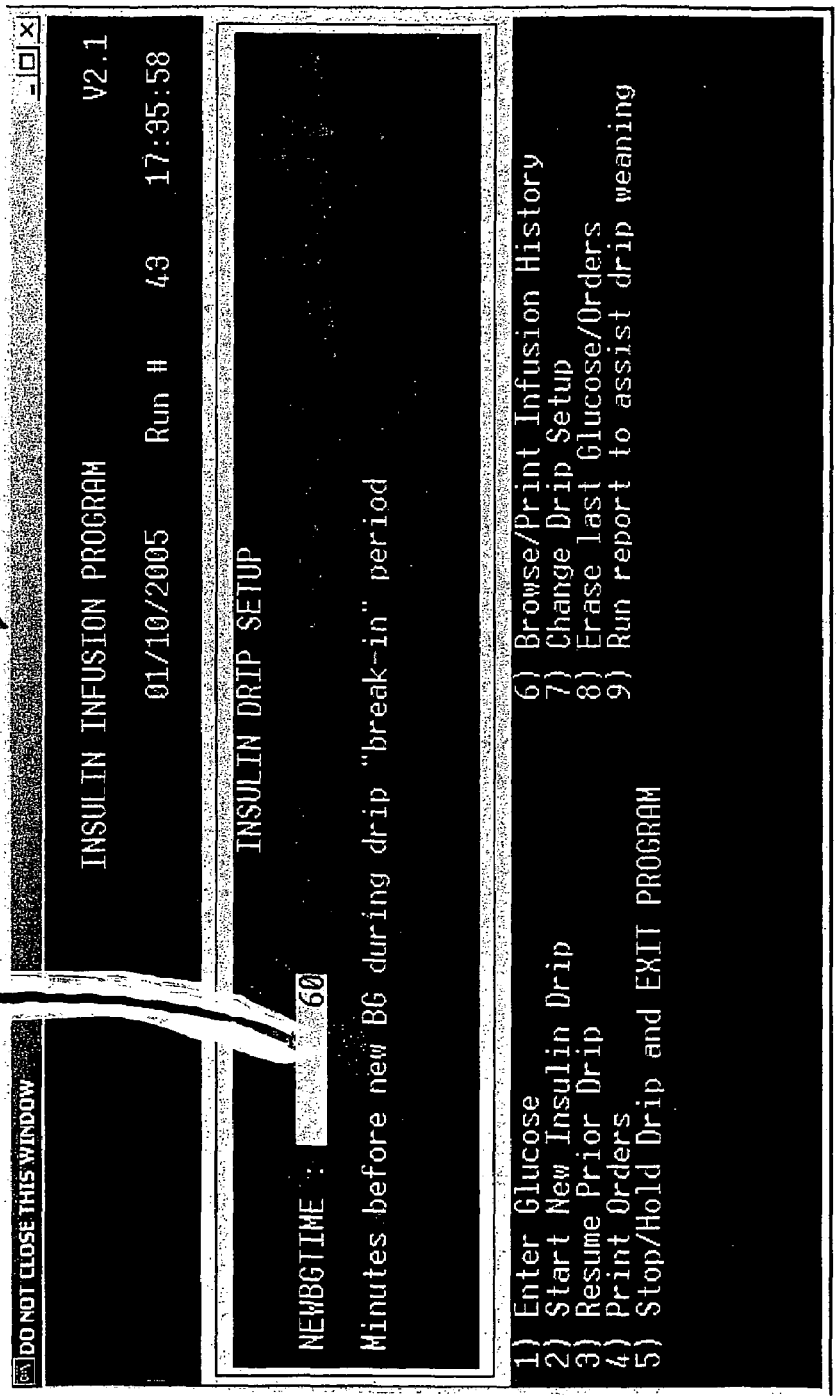

FIG. 10 illustrates a screen 120 in which an entry 122 specifies the time in minutes between BG level measurements, i.e., normal recheck interval, when the glucose measurements fall within the target range. FIG. 11 shows a screen 124 in which an entry 126 specifies the time in minutes for a modified recheck interval when a BG reading falls below the target range. FIG. 12 shows a representative screen 128 that calls for an entry 130 that defines the number of initial BG measurements that must be completed before the initial recheck interval reverts to the normal recheck interval. FIG. 13 illustrates a screen 132 that sets a particular initial recheck interval through an entry 134 for a "break-in" period of time when a new insulin drip is established for a patient.

Figure 14:
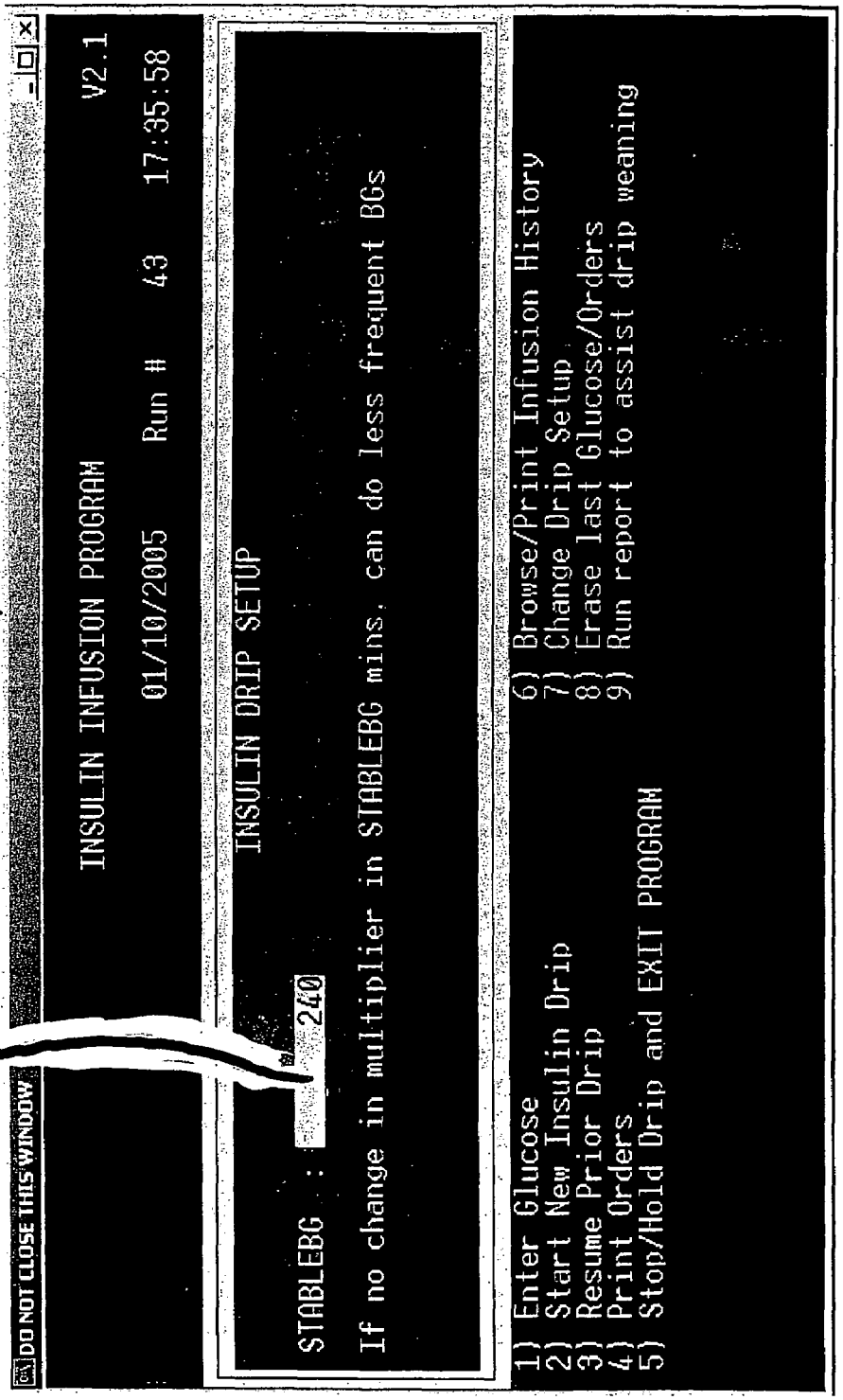
Figure 15:
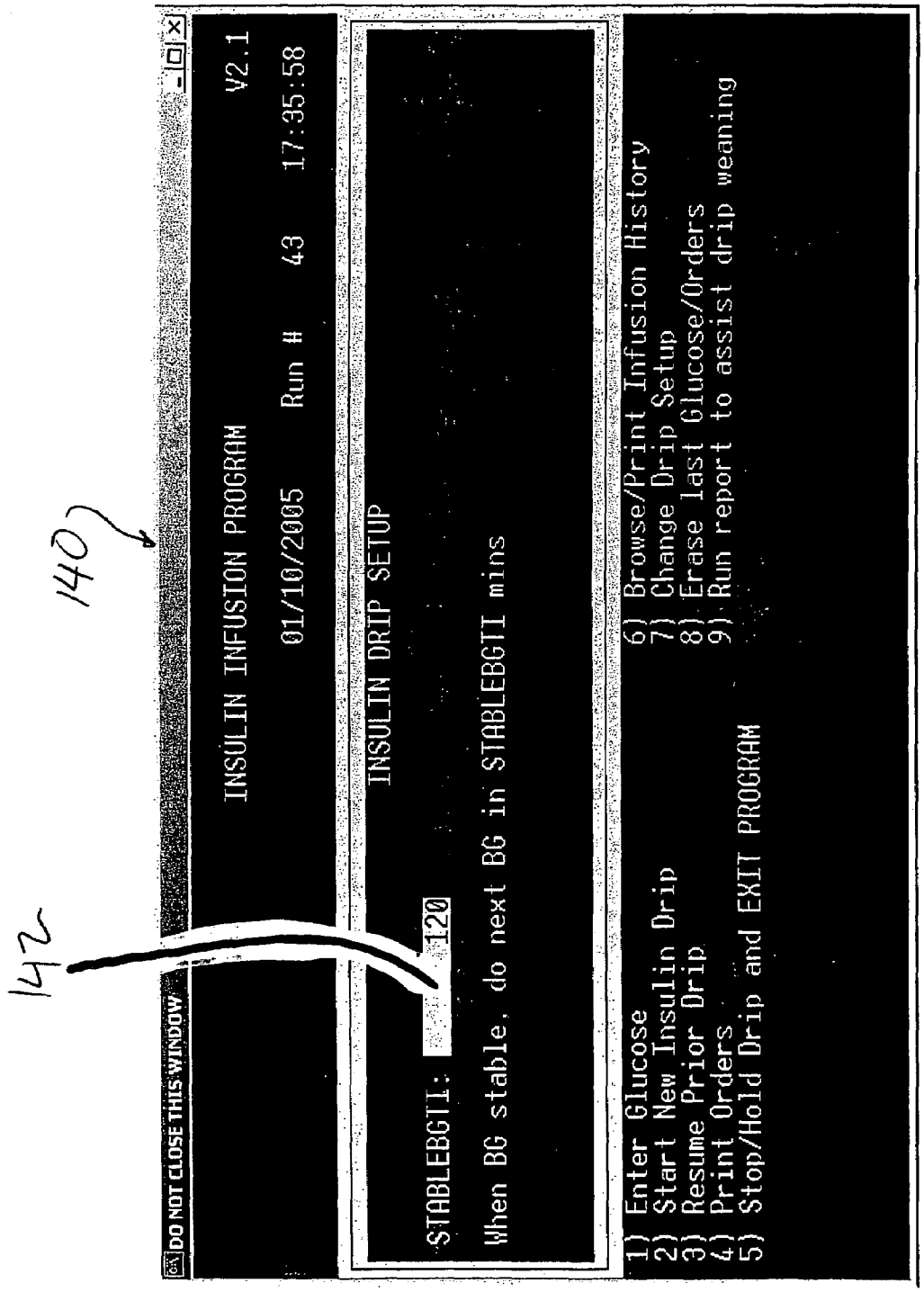
Figure 16:
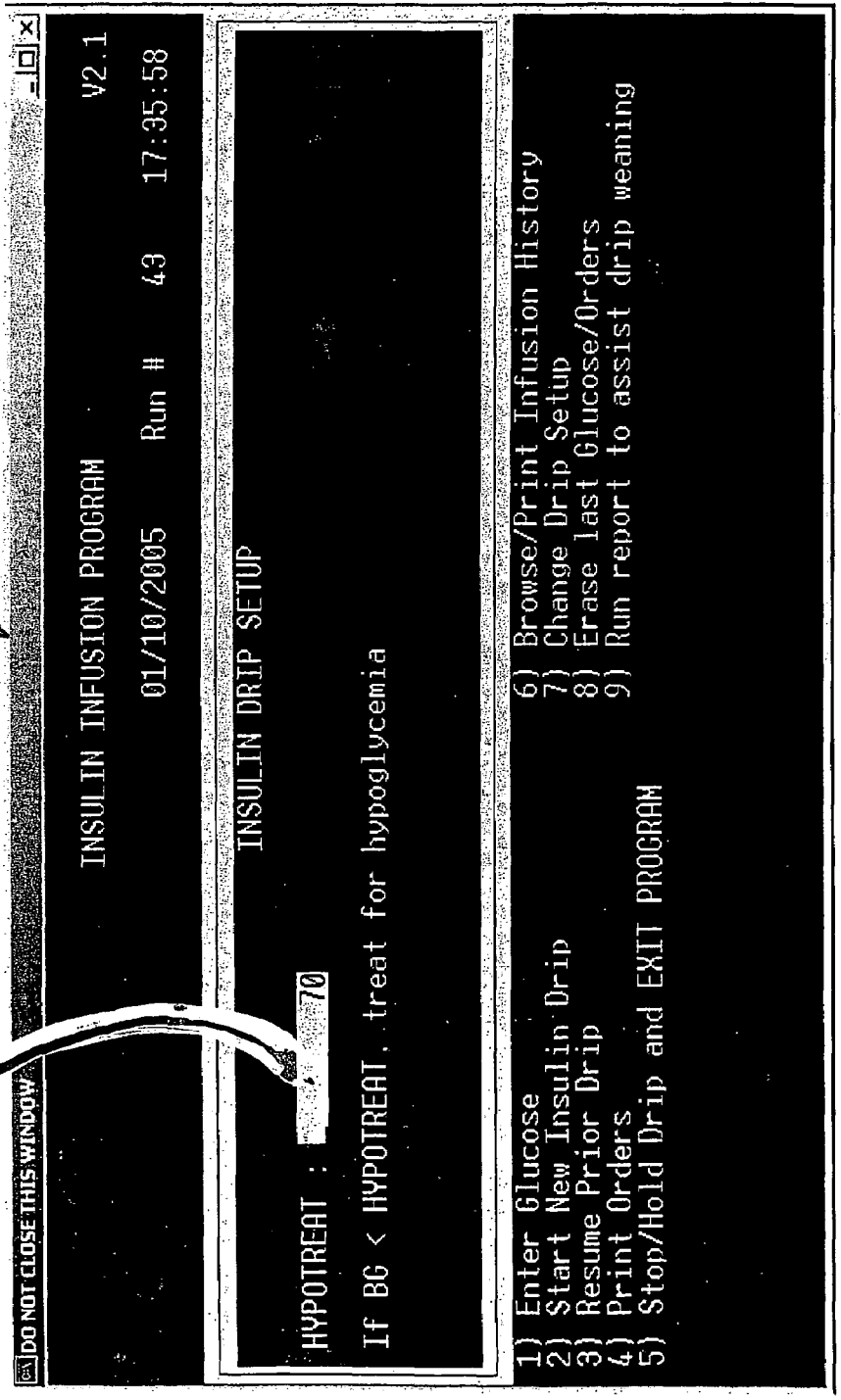
Figure 17:
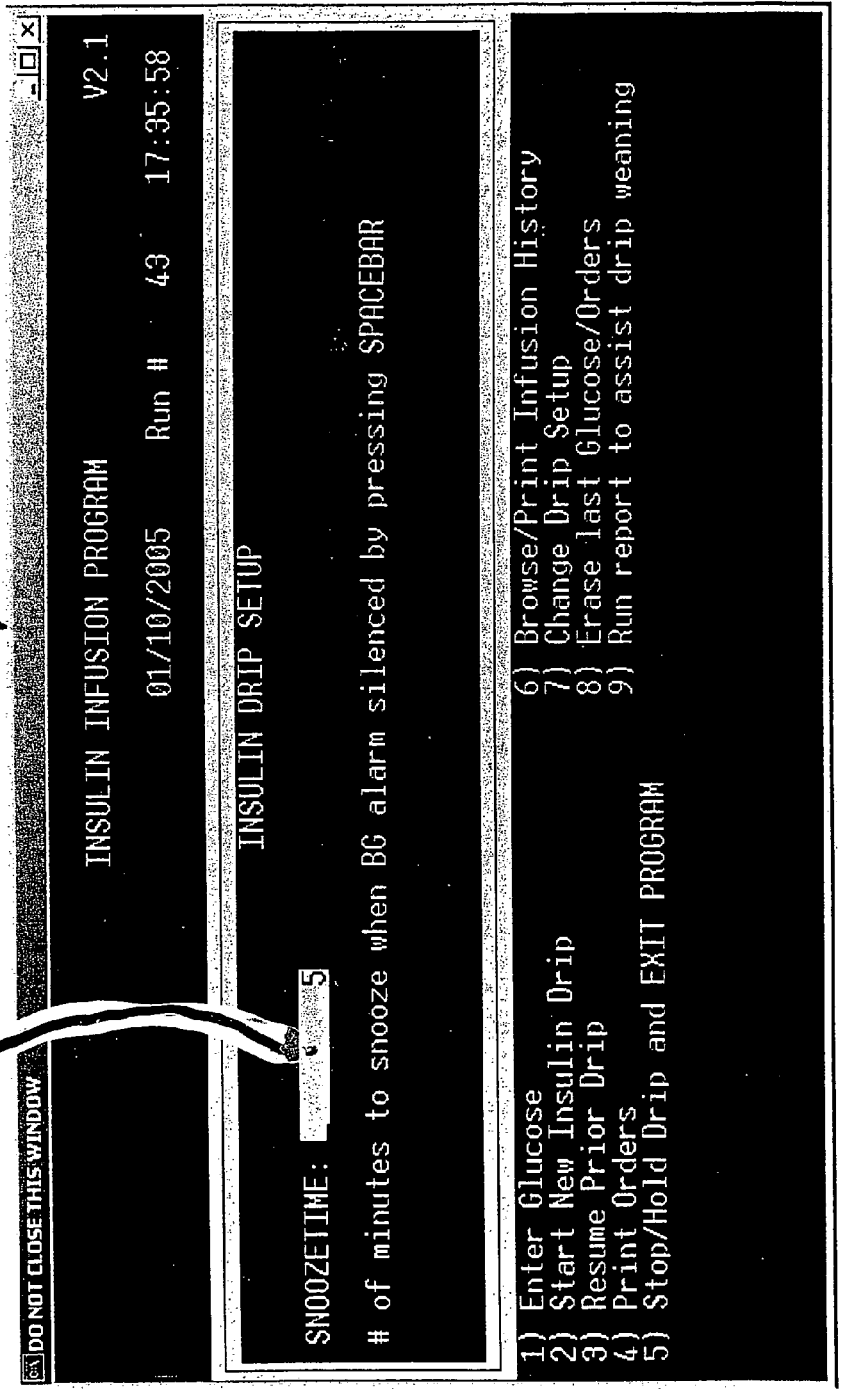
Figure 18:
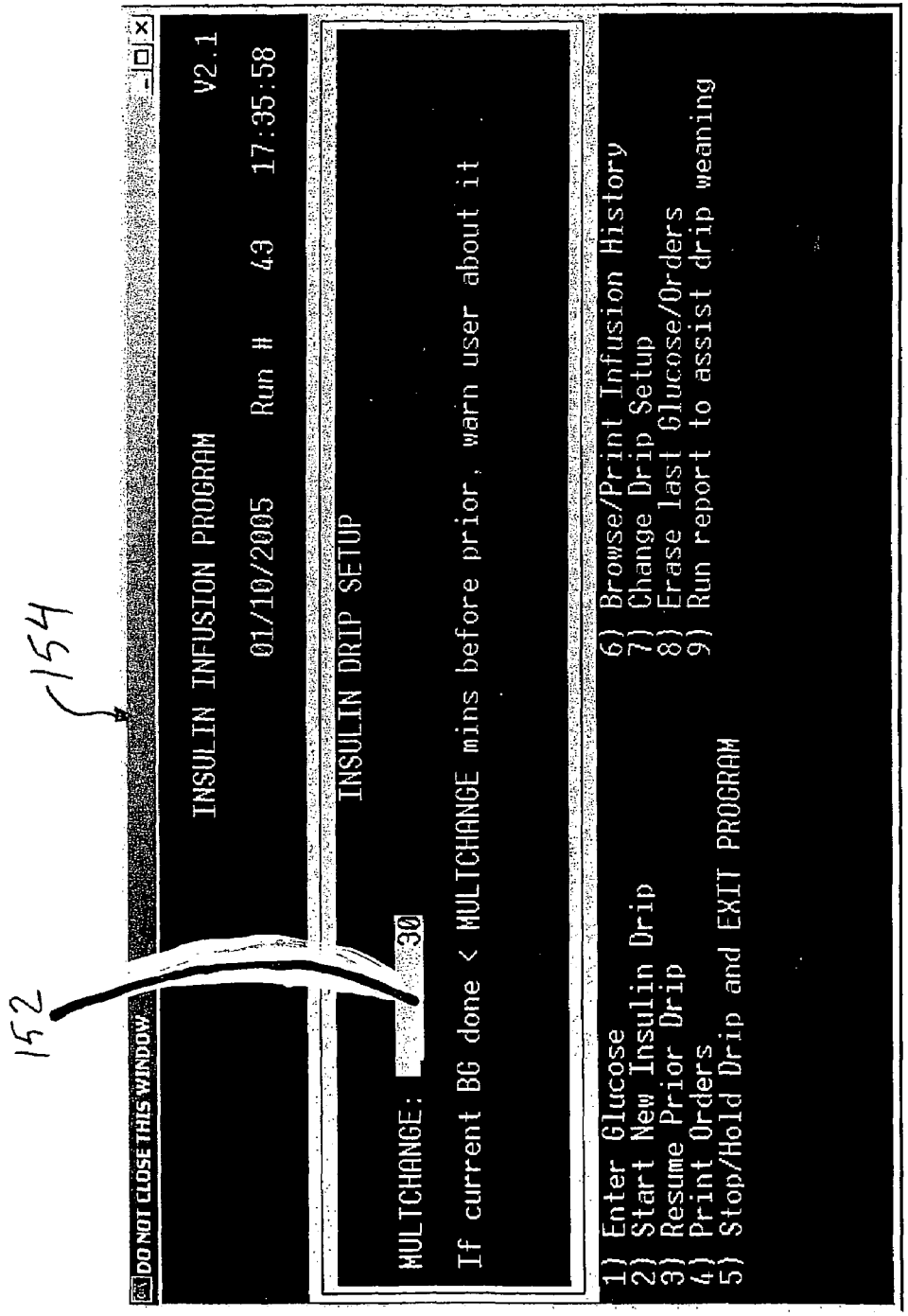

FIG. 14 illustrates a data entry 136 on screen 138 that specifies the number of minutes, over which the patient's BG measurement has been stable, necessary to allow system 10 to increase the recheck interval time. FIG. 15 thus shows in screen 140 via entry 142 the number of minutes that constitute the increased recheck interval. FIG. 16 shows a screen 144 in which a data entry 146 is requested to specify a low BG measurement that will cause an alert to be generated and/or displayed indicating that the patient should be treated for hypoglycemia, and calculating the amount of glucose (e.g., D-50 dextrose) solution needed to be administered to the patient. The alert, with the calculated glucose dosage, may be caused to be displayed at the patient's bedside and/or at a central monitoring station, and be of a visual and/or auditory nature, so that nurse 16 is appropriately notified to administer the glucose or dextrose solution to address the patient's hypoglycemia. The alert may also cause the necessary amount of the proper solution to be administered directly to the patient without any human intervention. FIG. 17 shows a screen 148 that allows an entry 150 of the number of minutes for a "snooze" interval that allows a nurse or caregiver to silence an audible alert or alarm for a limited time if it is not possible to immediately address the underlying condition that caused the alert. It is of course possible that in an automated system, such as system 70, for example, the alert is generated via a software program that causes the program to determine the proper treatment and automatically administer the necessary drugs or solutions to the patient.

Figure 19:
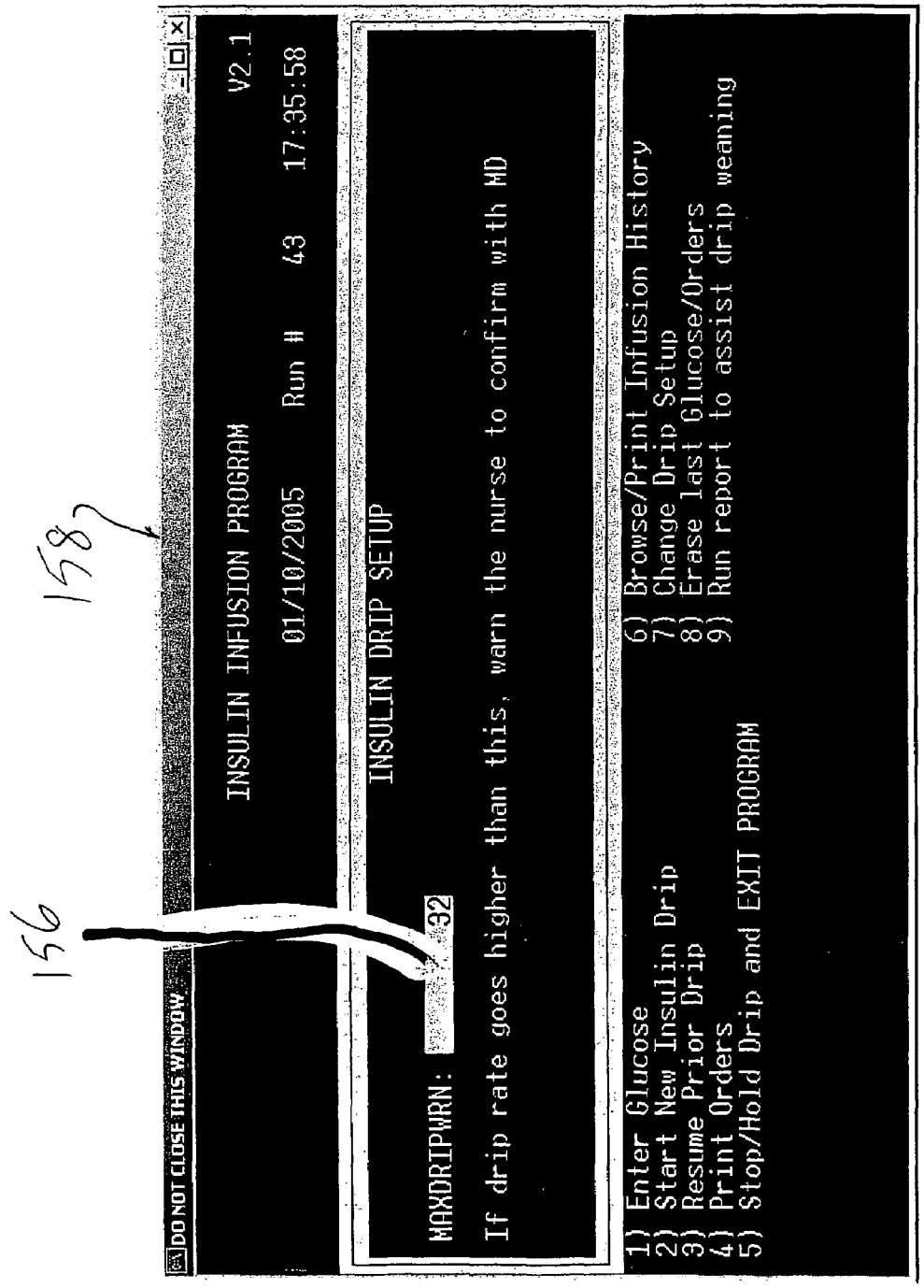
Figure 20:
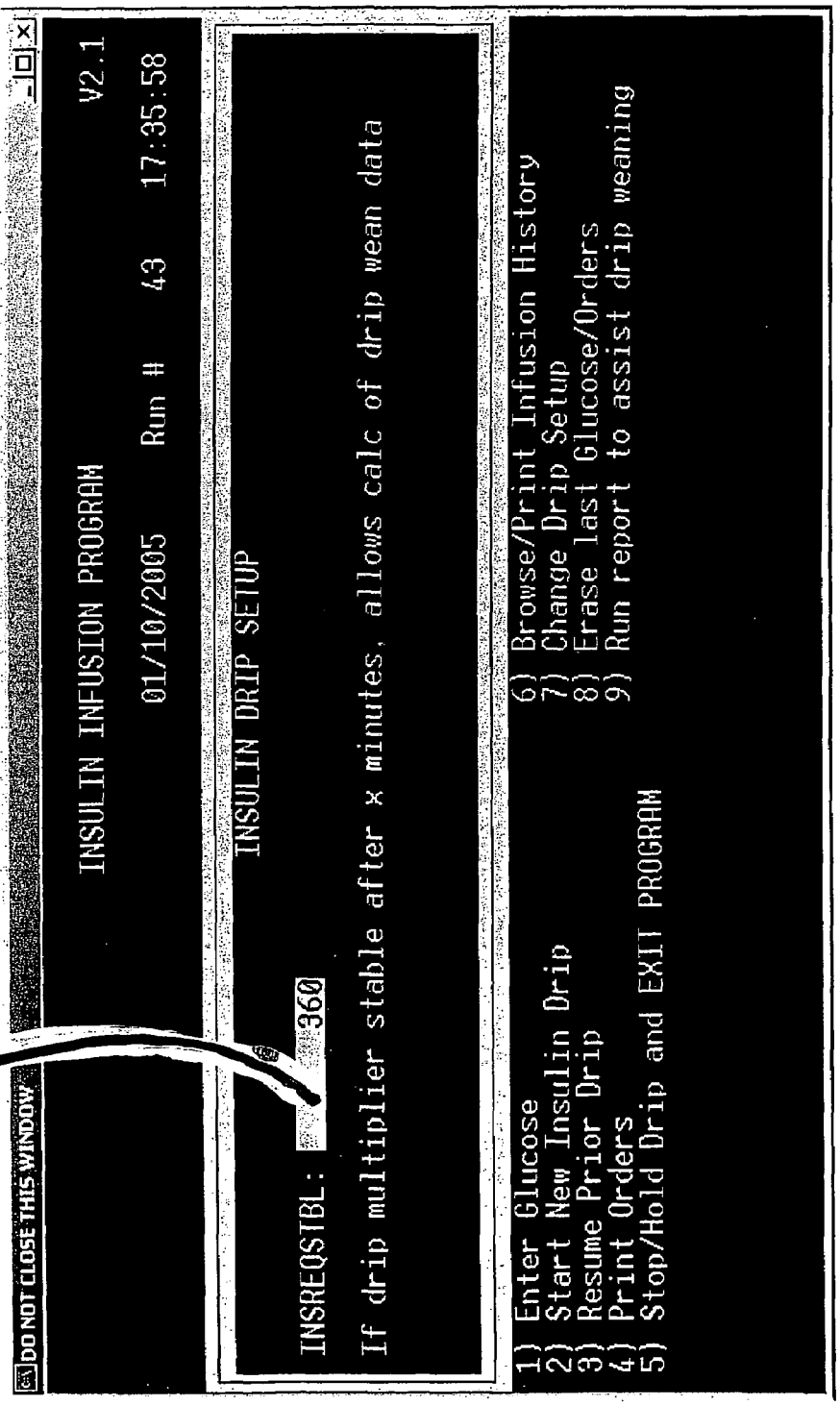
Figure 21:
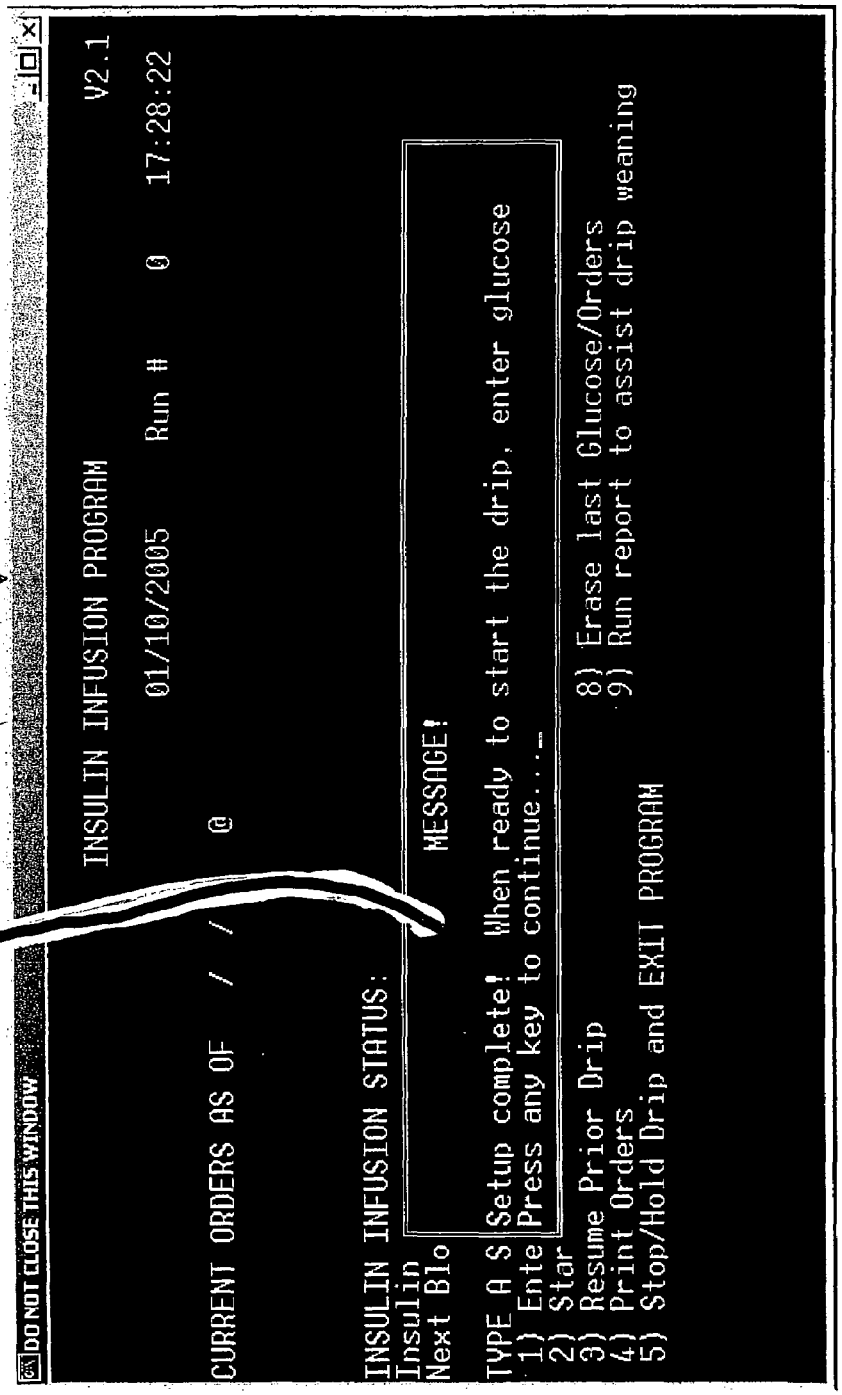

Additional information may also be entered and used by system 10, such as a time interval (in minutes) that will issue an alert or warning if a BG measurement has already been done during this interval. This is shown by entry 152 on screen 154 in FIG. 18 which is designed to protect against an inadvertent duplicate or incorrect patient data entry. A warning screen (not shown) would typically be displayed if a BG level were entered for a patient before this interval had passed or elapsed. FIG. 19 requests an entry 156, via screen 158, of a maximum drip rate that is allowed before an independent check or confirmation, such as by the patient's doctor, is needed to proceed. FIG. 20 illustrates a screen 160 that requires an entry 162 specifying the number of minutes over which a patient's measured BG level remains stable (e.g., within the normal range) before data relating to weaning the patient from an IV insulin drip to a subcutaneous insulin treatment can be determined or calculated. The screen 164 in FIG. 21 signifies via a message 166 that the insulin drip setup program has been completed, and that the patient's current BG measurement can now be entered.

Figure 22:
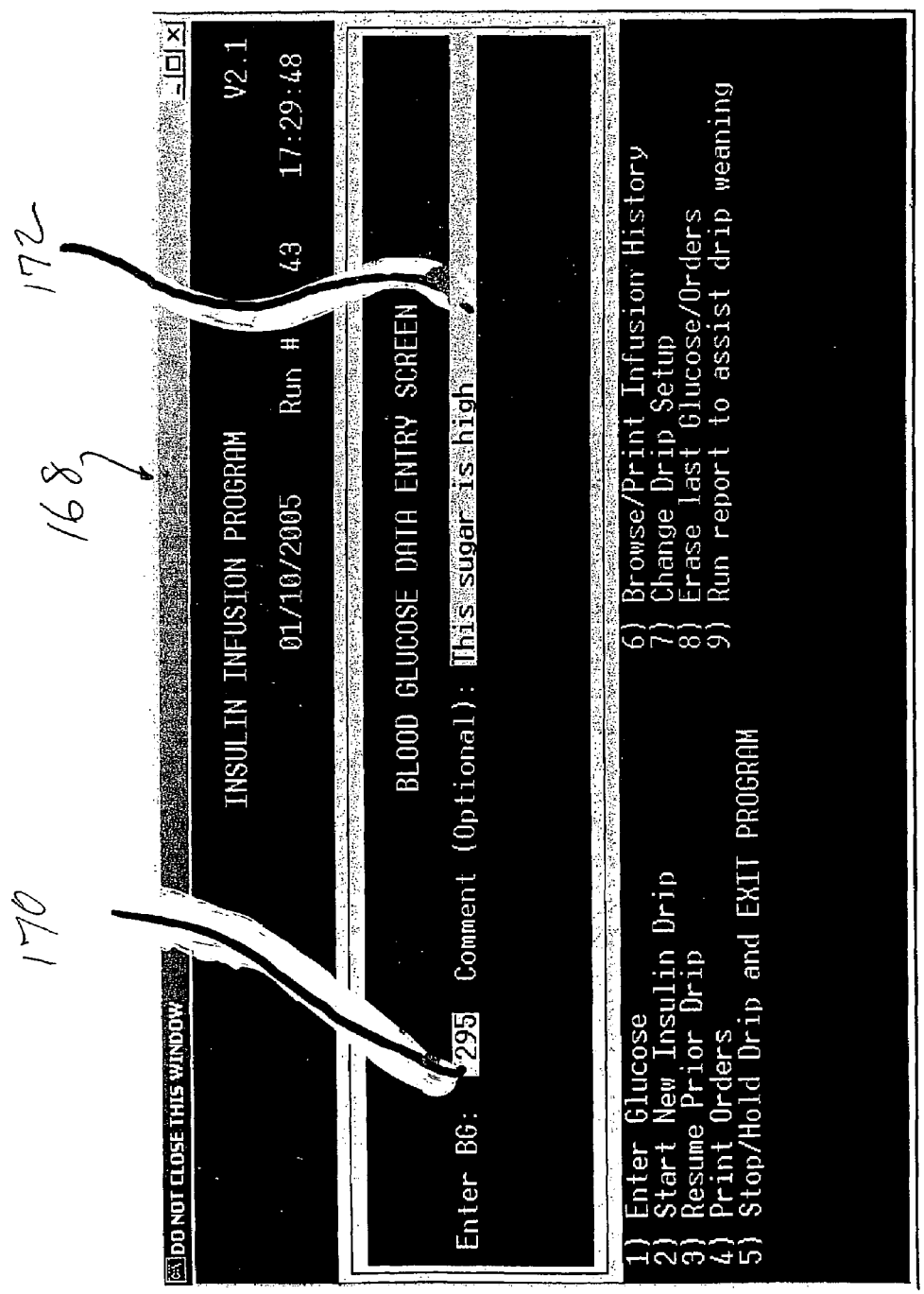
Figure 23:
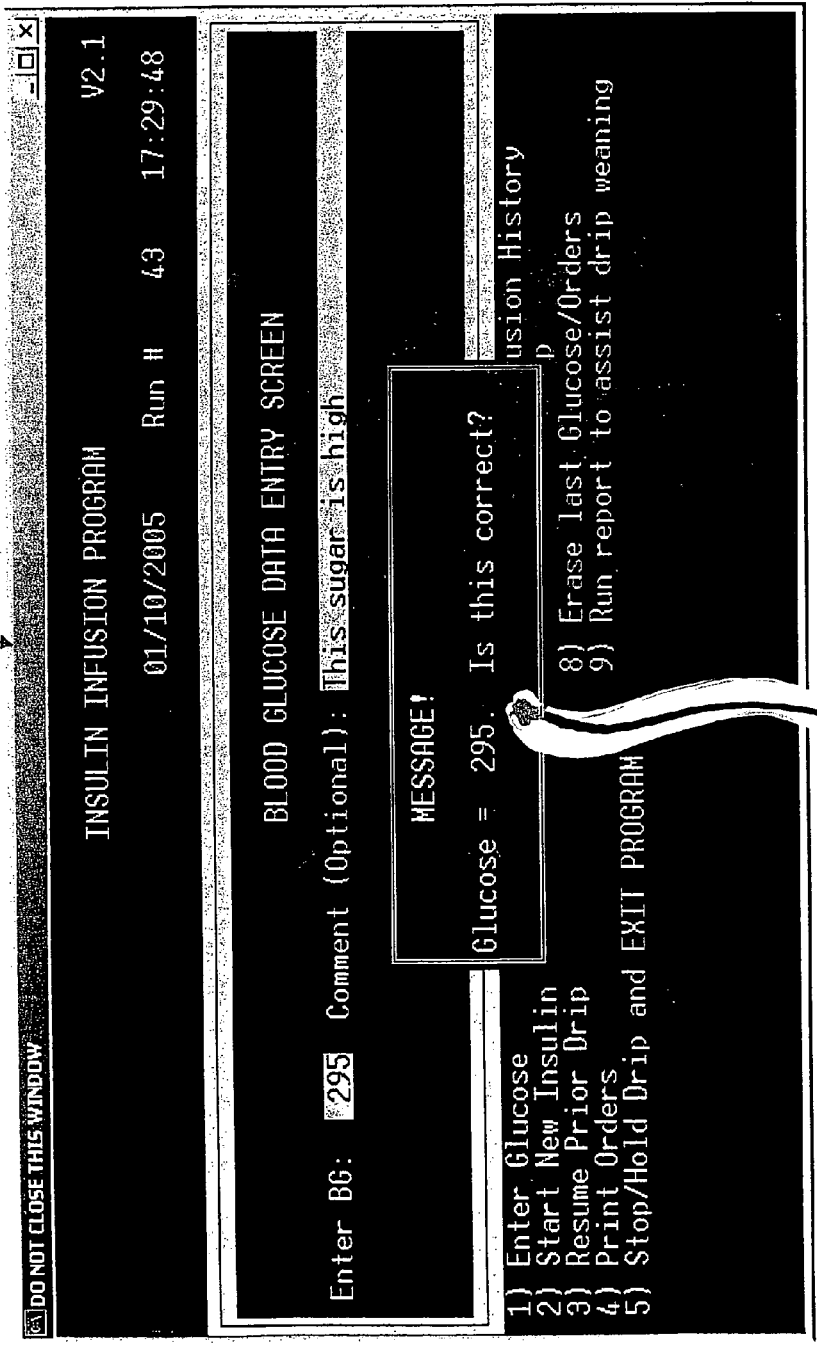

FIG. 22 shows a screen 168 in which an entry 170 indicates a BG level of 295 mg/dl for patient John Doe. A comment field 172 is also provided to enable a doctor, nurse, or other caregiver to record a comment or piece of information that may be useful to other caregivers during a following shift, for example. Comment field 172 is shown as indicating "This sugar is high." FIG. 23 further illustrates an alert message 174 which appears on screen 168 when the previously described BG level of 295 mg/dl is entered, thereby allowing a careful verification of the accuracy of the glucose measurement or, if the measurement accuracy cannot be positively established, a second blood measurement can be taken.

Figure 27:
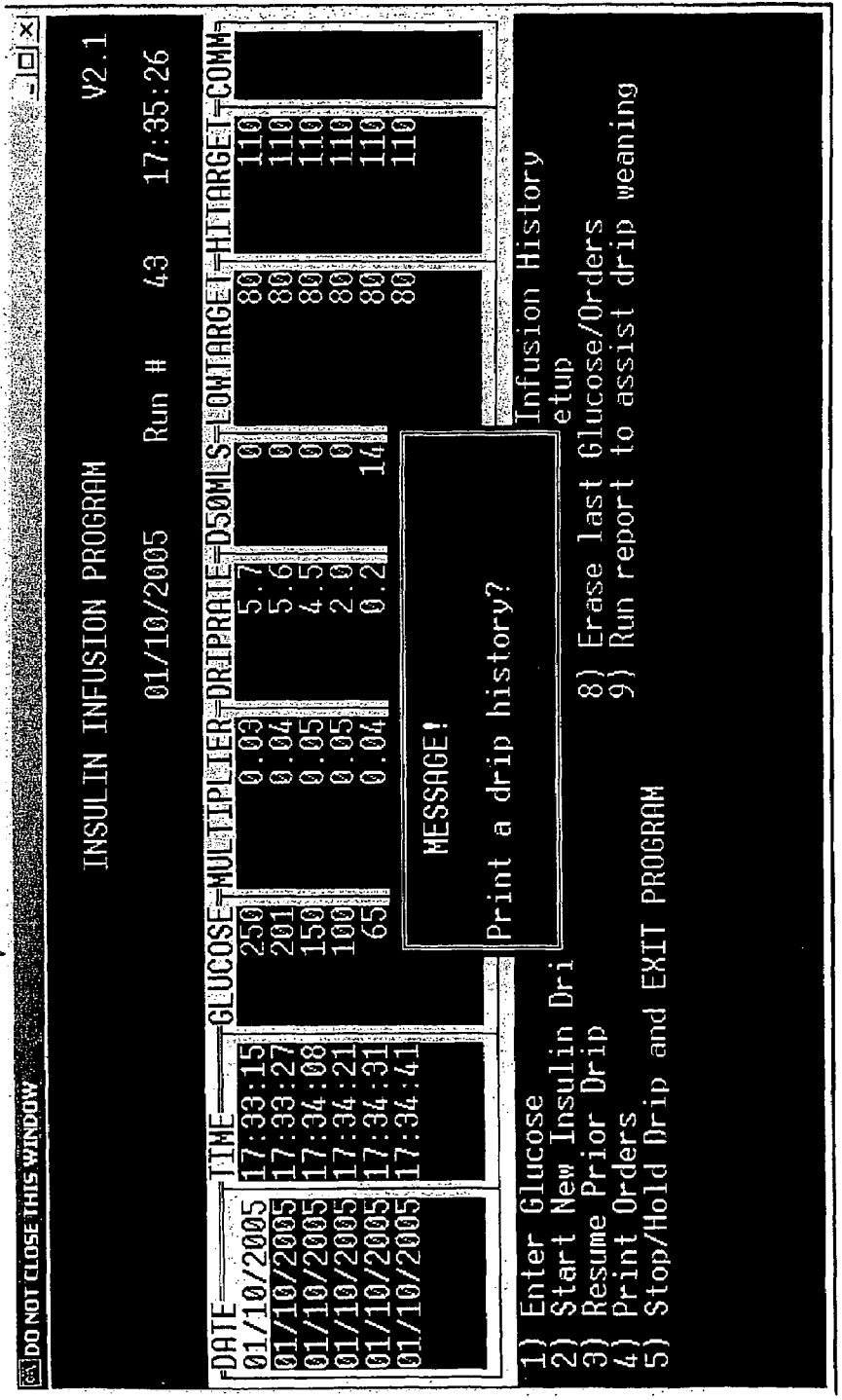

FIG. 24 shows a status screen 176 that appears once an IV insulin drip is established with patient or individual John Doe. Status screen 176 provides a summary of current BG measurement and treatment information concerning John Doe, such as insulin infusion drip rate, last BG reading, and the recheck interval. FIG. 25 shows a screen 178 that illustrates a historical summary chart for patient John Doe. FIG. 26 shows a screen 180 that provides information needed to wean patient John Doe from an IV insulin drip treatment to the administration of insulin subcutaneously. The information may include, as non-limiting examples, the time over which the current insulin drip rate has been able to maintain John Doe's BG at a stable level, the amount of insulin needed to cover a particular amount of dietary carbohydrate, and the effect on BG level of a particular dose of insulin. Lastly, FIG. 27 shows a screen 182 that is displayed when the action requesting a printed report is selected, in order to verify that the selected action is what was intended to be selected.

The previous description has been made based on treatment of hyperglycemic patients in an in-patient medical/surgical setting, such as a hospital or nursing home, as the novel features of the invention lend themselves particularly well to a critical or intensive care setting. The scope of the invention, however, is not limited to an in-patient environment. Significant advantages can also be realized by ambulatory or otherwise healthy individuals with diabetes through the use of, for example, periodic or continuous blood glucose measurement devices and an insulin pump. The manner in which such as system, incorporating one or more embodiments of the present invention, could provide automatic blood glucose measurement and administration of proper insulin amounts while still maintaining sufficient safeguards to protect against an inadvertent application of an incorrect insulin dose due to an equipment malfunction or some incident of human error. Changes in set-up or default settings can also be made to accommodate patients who encounter wide swings in their BG measurements (e.g., brittle diabetics), or those changes could be made in response to, or in anticipation of, specific events, such as when a hyperglycemic individual intends to engage in an activity that would otherwise cause BG levels to vary beyond normal level, e.g., running a marathon.

While the invention has been illustrated and described in detail in the drawing and foregoing description, the same is to be considered as illustrative and not restrictive in character, it being understood that only the preferred embodiment has been shown and described and that all changes, modifications and equivalents that come within the spirit of the inventions disclosed are desired to be protected. The articles "a", "an", "said" and "the" are not limited to a singular element, and include one or more such elements.

What is claimed is:

1. A system for maintaining a blood glucose level in an individual comprising:

setup means for establishing a desired range of blood glucose levels for said individual;

measuring means for determining a blood glucose level for said individual;

calculating means responsive to said blood glucose level for determining a proper glucose dosage amount for said individual when said blood glucose level is below said desired range and for determining a proper insulin dosage amount for said individual when said blood glucose level is above said desired range;

delivery means for administering at least one of said glucose dosage amount or said insulin dosage amount to said individual;

evaluation means responsive to said blood glucose level for determining a time interval for said individual after which said individual's blood glucose level is to be re-measured;

timing means for generating a signal when said time interval has elapsed; and estimating means responsive to said calculated glucose dosage amount or said calculated insulin dosage amount, and to at least one criteria associated with said individual, for estimating the accuracy of said calculated dosage amount.

2. The system described in claim 1, further comprising notification means for generating an alert signal when said estimated accuracy is below a predetermined level.

3. The system described in claim 2, wherein said alert signal is auditory.

* * * * *